United States Patent
Mohamad Hani et al.

(10) Patent No.: US 9,532,744 B2
(45) Date of Patent: Jan. 3, 2017

(54) METHODOLOGY FOR DETERMINING CONCENTRATION OF THE TYPES OF MELANIN PIGMENT IN THE SKIN

(71) Applicant: INSTITUTE OF TECHNOLOGY PETRONAS SDN BHD, Tronoh (MY)

(72) Inventors: Ahmad Fadzil Mohamad Hani, Tronoh (MY); Hermawan Nugroho, Tronoh (MY)

(73) Assignee: INSTITUTE OF TECHNOLOGY PETRONAS SDN BHD, Tronoh (MY)

( * ) Notice: Subject to any disclaimer, the term of this patent is extended or adjusted under 35 U.S.C. 154(b) by 223 days.

(21) Appl. No.: 14/372,679

(22) PCT Filed: Nov. 26, 2012

(86) PCT No.: PCT/MY2012/000287
§ 371 (c)(1),
(2) Date: Jul. 16, 2014

(87) PCT Pub. No.: WO2013/081447
PCT Pub. Date: Jun. 6, 2013

(65) Prior Publication Data
US 2015/0057552 A1      Feb. 26, 2015

(30) Foreign Application Priority Data

Nov. 30, 2011  (MY) .......................... PI 2011005800

(51) Int. Cl.
| | |
|---|---|
| *A61B 6/00* | (2006.01) |
| *A61B 5/00* | (2006.01) |
| *G01J 3/02* | (2006.01) |
| *G01J 3/28* | (2006.01) |

(52) U.S. Cl.
CPC ............. *A61B 5/443* (2013.01); *A61B 5/0075* (2013.01); *A61B 5/0077* (2013.01); *G01J 3/0208* (2013.01); *G01J 3/0237* (2013.01); *G01J 3/2823* (2013.01); *G01J 2003/2826* (2013.01)

(58) Field of Classification Search
CPC ..... A61B 5/443; A61B 5/0075; A61B 5/0077; G01J 3/0208; G01J 3/0237; G01J 3/2823; G01J 2003/2826
USPC ................................................ 600/473–480
See application file for complete search history.

(56) References Cited

U.S. PATENT DOCUMENTS

| | | | |
|---|---|---|---|
| 7,467,870 B2 | 12/2008 | van de Kraats et al. | |
| 7,888,659 B2 | 2/2011 | Scholz et al. | |
| 2003/0002028 A1* | 1/2003 | Rice ................... | G01N 21/4795 356/39 |
| 2005/0049467 A1 | 3/2005 | Stamatas et al. | |

(Continued)

OTHER PUBLICATIONS

International Search Report of PCT/MY2012/000287, dated Apr. 16, 2013, 2 pages total.

(Continued)

*Primary Examiner* — Sanjay Cattungal
(74) *Attorney, Agent, or Firm* — Hamre, Schumann, Mueller & Larson, P.C.

(57) ABSTRACT

The present invention relates generally to a methodology of determining the concentration of the types of melanin, either eumelanin or pheomelanin, in the skin wherein the process for such determination is non-invasive and based on digital signal and image analysis of hyperspectral sensing and multi-spectral data.

6 Claims, 7 Drawing Sheets

(56) References Cited

U.S. PATENT DOCUMENTS

| | | |
|---|---|---|
| 2006/0020183 A1 | 1/2006 | Pershing et al. |
| 2008/0075340 A1 | 3/2008 | Cotton et al. |
| 2009/0076396 A1* | 3/2009 | Yaroslavsky ........ A61B 5/0068 600/476 |
| 2010/0042004 A1* | 2/2010 | Dhawan ............... A61B 5/0059 600/476 |

OTHER PUBLICATIONS

Cotton et al., "Developing a predictive model of human skin colouring," Proceedings of SPIE, vol. 2708, Medical imaging 1996, pp. 814-825.

Diffey et al., "A method for predicting the phototoxicity of non-steroidal anti-inflammatory drugs," Br. J. clin. Pharmac., 1983, vol. 16, pp. 633-638.

Diffey et al., "The UVB content of 'UVA fluorescent lamps' and its erythemal effectiveness in human skin," Phys. Med. Biol., 1983, vol. 28, No. 4, pp. 351-358.

Fadzil et al.,"Independent component analysis for assessing therapeutic response in vitiligo skin disorder," J Med Eng Technol 2009; 33(2):101-9.

Jung et al., "Characterization of port wine stain skin erythema and melanin content using cross-polarized diffuse reflectance imaging," Lasers in Surgery and Medicine, 2004, vol. 34, pp. 174-181.

Chafekar et al., "Pressure distribution on a semi-circular concave surface impinged by a single row of circular jets," Proceedings of the 35th National Conference on Fluid Mechanics and Fluid Power, Bangalore. 2008, 9 pages total.

Takiwaki et al., "The degrees of UVB-induced erythema and pigmentation correlate linearly and are reduced in a parallel manner by topical anti-inflammatory agents," The Journal of Investigative Dermatology, 1994, vol. 103, No. 5, pp. 642-646.

Tsumura et al., "Independent component analysis of skin color image," JOSA A 16.9 (1999), 18 pages total.

Ojima et al., "Application of image-based skin chromophore analysis to cosmetics," Journal of Imaging Science and Technology 48.3 (2004), 16 pages total.

Jalil, "Multispectral image processing applied to dermatology," Le2i laboratory, Université de Bourgogne, A thesis submitted for the Degree of MSc Erasmus Mundus in Vision and Robotics (VIBOT), 2008, abstract only, 3 pages.

Levenson et al., "Multispectral imaging in biology and medicine: slices of life," Cytometry Part A 69A: 748-758 (2006).

Alaluf et al., "Dietary carotenoids contribute to normal human skin color and UV photosensitivity," J. Nutr., 2002, vol. 132, No. 3, pp. 399-403.

Cotton, "A noninvasive skin imaging system," 1997, School of Computer Science, University of Birmingham, Birmingham, B15 2TT, UK, 15 pages total.

Tsumura et al., "Mapping pigmentation in human skin by multi-visible-spectral imaging by inverse optical scattering technique," Journal of Imaging Science and Technology 45, No. 5, 2001, pp. 444-450.

Anderson et al., "The optics of human skin," The Journal of Investigative Dermatology, 1981, vol. 77, No. 1, pp. 13-19.

Takiwaki, "Measurement of skin color: practical application and theoretical considerations," The Journal of Medical Investigation, 1998, vol. 44, pp. 121-126.

Tsumura et al., "Image-based skin color and texture analysis/synthesis by extracting hemoglobin and melanin information in the skin," ACM Transactions on Graphics (TOG). vol. 22. No. 3. ACM, 2003, 10 pages total.

Thody et al., "Pheomelanin as well as eumelanin is present in human epidermis," The Journal of Investigative Dermatology, 1991, vol. 97, No. 2, pp. 340-344.

Meglinski et al., "Quantitative assessment of skin layers absorption and skin reflectance spectra simulation in the visible and near-infrared spectral regions," Physiological Measurement, 2002, 23 (4): 741-753.

Clarys et al., "Skin color measurements: comparison between three instruments the Chromameter®, the DermaSpectrometer®, and the Mexameter®," Skin Research and Technology, 2000, vol. 6, pp. 230-238.

Claridge et al., "Spectrophotometric intracutaneous imaging (SIAscopy): method and clinical applications," Chapter 37 in Handbook of Non-Invasive Methods and the Skin ($2^{nd}$ ed)., 2006, 11 pages total.

Doi et al., "Spectral estimation of human skin color using the Kubelka-Munk theory," Proceedings of SPIE-IS&T Electronic Imaging, SPIE vol. 5008, 2003, pp. 221-228.

Ito et al., "Quantitative analysis of eumelanin and pheomelanin in hair and melanomas," The Journal of Investigative Dermatology, 1983, vol. 80, No. 4, pp. 268-272.

Shimada et al., "Explanation of human skin color by multiple linear regression analysis based on the modified Lambert-Beer law," Optical Review, 2000, vol. 7, No. 4, pp. 348-352.

Lieneke et al., "Colour evaluation in scars: tristimulus colorimeter, narrow-band simple reflectance meter or subjective evaluation?," Burns, 2004, vol. 30, pp. 103-107.

Prahl et al., "A Monte Carlo model of light propagation in tissue," Dosimetry of Laser Radiation in Medicine and Biology, SPIE Institute Series vol. IS 5, 1989, pp. 102-111.

Parsad et al., "Eumelanin and phaeomelanin contents of depigmented and repigmented skin in vitiligo patients," British Journal of Dermatology, 2003, vol. 149, pp. 624-626.

Meglinsky et al., "Modelling the sampling volume for skin blood oxygenation measurements," Med. Biol. Eng. Comput., 2001, vol. 29, pp. 44-50.

Wang et al., "MCML—Monte Carlo modeling of light transport in multi-layered tissues," Computer Methods and Programs in Biomedicine, 1995, vol. 47, pp. 131-146.

\* cited by examiner

METHODOLOGY FOR DETERMINING CONCENTRATION OF THE TYPES OF MELANIN PIGMENT IN THE SKIN

1. TECHNICAL FIELD OF THE INVENTION

The present invention relates generally to a methodology of determining the concentration of the types of melanin pigments, either eumelanin and pheomelanin, in the skin wherein the process for such determination is non-invasive and based on digital signal and image analysis of hyperspectral sensing and multi-spectral data.

2. BACKGROUND OF THE INVENTION

Skin pigmentation disorders are conditions that cause the skin colour to appear lighter or darker than normal. The principal determinant of skin colour is the melanin pigment and variation in the amount and distribution of melanin in the skin are the basis of the three principal skin colours namely black, brown and white. Abnormality of melanin production causes skin pigmentation disorders.

There are two main categories of skin pigmentation disorders namely hypo-pigmentation and hyper-pigmentation. Hypo-pigmentation is the loss of skin colour caused by melanin depletion whilst hyper-pigmentation is the darkening of area of skin caused by increased melanin. Albinism and vitiligo are examples of hypo-pigmentation and melasma and freckles are examples of hyper-pigmentation. Hypo-pigmentation may be caused by melanocyte production being impaired for instance in a serious accident where most of the pigment producing layers of the upper skin would be damaged. Melanocytes make melanin, the pigment that gives the skin its color. If melanocytes production is impaired, so is the skin's ability to produce darker skin tones. Hyper-pigmentation may be caused by sun damage, inflamation or other skin injuries. Current treatment for hypo-pigmentation is typically carried out by various methods such as photochemotheraphy, topical corticosteroids, topical immuno-modulators, synthetic vitamin D3 analogues, therapy and a plethora of surgical techniques. Current treatment for hyper-pigmentation on the other hand is by bleaching and photochemotheraphy. In order to alleviate health risks associated to invasive treatments, tools for measuring melanin and other pigment levels that have been introduced and developed to treat skin pigmentation disorders have the tendency to be non-invasive in nature. Amongst such non-invasive measurement tools are namely camera to capture RGB image (Takiwaki et al 1994; Takiwaki et al 1998, Jung et al 2004); Chromameter to obtain colour data (P. Clarys et al 2001; Alaluf et al 2002, Nayan et al 2008), Derma spectrometer to obtain colour data (P. Clarys et al 2001; Lieneke et al 2003), Multispectral camera to capture multispectral image (Moncrieff et al 2002, Luadi et al 2006, Bushra J. 2008).

In the above non-invasive treatment, changes to the skin surface colour as a response to treatment takes time. To assess the efficacy of different treatment modalities of skin pigmentation disorder, a considerable time is needed for skin surface colour to change. This is because the measurement process (under Physician's Global Assessment [PGA] framework) only refers to the visual conditions of the skin surface and does not assess the conditions of the underlying skin layers and pigments. Moreover the PGA protocol is not yet standardised.

Hence the delay caused by observing the changes to the skin surface colour as a response to treatment is not an effective solution and a better more effective method has to be researched upon. It has been known that there are two types of melanin namely eumelanin and pheomelanin which are important in the understanding of the underlying causes of skin pigmentation disorders which would greatly facilitate analysis of pigmentation disorder reliably. Eumelanin is found in people with dark skin and gives a black or brown colour whilst pheomelanin is found in people with light and dark skin and gives a red and yellow colour [Thody A. J et al. 1991]. From the above literature, although there are many non-invasive tools for measuring skin pigments, there is currently no validated in vivo method that is non-ionising and non-invasive to accurately measure melanin types and quantities to be used in assessing severity of skin pigmentation disorder and treatment efficacies. There is presently no known methods and devices to classify and determine the types of melanin namely eumelanin and pheomelanin save for the biochemical method [A. J. Thody et al 1991; Ito 2003] which is unfortunately invasive in nature as skin biopsy is conducted for chemical analysis of skin samples. This biochemical method is able to classify and measure the types of melanin (eumelanin and pheomelanin) which is important in understanding the underlying causes of skin pigmentation disorder but being invasive in nature would carry with it certain health risks or perhaps discomfort, no matter how minor the treatment is.

The tools for measuring melanin and other pigment levels enables quantification of the level of the melanin pigment types in the skin but it would not be of assistance in analysing the severity of skin pigmentation disorder. For this reason skin pigmentation models are developed not only to give a detailed understanding on the role of melanin pigment types in human skin but also to develop an objective method for the classification of melanin pigment types in human skin. Present skin pigmentation models for analysing skin have revolved around analysing the skin dermis solely; the skin dermis together with epidermis; the skin dermis together with the epidermis and skin pigment (melanin); the skin dermis, together with epidermis and skin pigment (melanin and other pigments). Skin pigmentation models for analysing the skin dermis solely are the Empirical (Kulbelka Munk) model disclosed by Anderson et al 1981 and the Simulated (Monte Carlo) model by Prahl et al 1989. Skin pigmentation models for analysing the skin dermis together with epidermis are the Empirical (Kulbelka Munk) model disclosed by, Wan et al 1981 and Diffey et al 1983 and the Simulated (Monte Carlo) model by Wang et al 1995. Skin pigmentation models for analysing the skin dermis together with epidermis and skin pigment (melanin) are the Empirical (Kulbelka Munk) model disclosed by Cotton et al 1996, Cotton et al 1997. Skin pigmentation models for analysing the skin dermis together with epidermis and skin pigment (melanin and other pigments) are the Empirical (Kulbelka Munk) model as disclosed by Do et al 2003; the Simulated (Monte Carlo) model disclosed by Tsumura et al 2000, Meglinsky et al 2001, Shimada et al 2003 and Meglinsky et al 2007; and the Statistical (ICA) model by Tsumura et al 1999, Tsumura et al 2004 and Fadzil et al 2009. However to date there are no new skin pigmentation models that can analyse skin dermis epidermis as well as the melanin pigment types namely eumelanin and pheomelanin which as is known is vital in providing valuable information on the condition of skin enabling reliable analysis on the severity of skin pigmentation disorder for proper and expedited treatment.

It would hence be extremely advantageous if the above shortcoming is alleviated by having a non-invasive method for determining the level of the melanin types namely eumelanin and pheomelanin in order to facilitate the developing of human skin pigmentation computation model using digital signal and image analysis of hyperspectral sensing and multispectral data.

3. SUMMARY OF THE INVENTION

Accordingly, it is the primary aim of the present invention to provide a method for determining the concentration of the types of melanin pigment in the skin that is non-invasive;

It is yet another object of the present invention to provide a method for determining the concentration of the types of melanin pigment in the skin that enables reliable analysis of the severity of skin pigmentation disorder;

It is yet another object of the present invention to provide a method for determining the concentration of the types of melanin pigment in the skin which is non-ionising.

It is a further object of the present invention to provide a method for determining the concentration of the types of melanin pigment in the skin enabling the development of a skin pigmentation model that is capable of giving a detailed understanding on the role of melanin pigment types in human skin.

Yet another object of the present invention is to provide a method for determining the concentration of the types of melanin pigment in human skin enabling the development of a skin pigmentation model that is capable of facilitating development of an objective method for the classification of melanin pigment types in human skin.

Yet a further object of the present invention is to provide a method for determining the concentration of the types of melanin pigment in human skin capable of developing a human skin pigmentation computation model using digital signal and image analysis of hyperspectral sensing and multispectral data.

Other and further objects of the invention will become apparent with an understanding of the following detailed description of the invention or upon employment of the invention in practice.

According to a preferred method of the present invention there is provided,

Methodology for determining the concentration of melanin pigment in human skin comprising steps of, measuring actual spectral reflectance (12) of skin (10) using a visible light intensity sensing device (2) and recording this multi-spectral data using a recording device (8) for retrieval when required;

selecting initial concentration of a type of melanin pigment and recording simulated spectral reflectance (18) using Monte Carlo simulation;

comparing and measuring the difference between data collected from the said visible light intensity sensing device (2) and data simulated from the Monte Carlo simulation;

determining the difference between the two sets of data;

estimating the concentration of a selected type of melanin pigment if the difference is smaller than an acceptable level;

altering the concentration of the selected type of melanin pigment and repeating the process from the spectral reflectance (18) using Monte Carlo simulation if the difference is larger than an acceptable level;

repeating the process until the difference is smaller than an acceptable level and then estimating the concentration of a selected type of melanin pigment.

4. BRIEF DESCRIPTION OF THE DRAWINGS

Other aspect of the present invention and their advantages will be discerned after studying the Detailed Description in conjunction with the accompanying drawings in which:

FIGS. 4-A to 4-C show graphic representations of skin absorption profile of different chromophores.

5. DETAILED DESCRIPTION OF THE DRAWINGS

Throughout this document, unless otherwise indicated to the contrary, the terms "comprising", "consisting of" and the like are to be construed as non-exhaustive, or in other words, as meaning "including, but not limited to".

In the following detailed description, numerous specific details are set forth in order to provide a thorough understanding of the invention. However, it will be understood by those or ordinary skill in the art that the invention may be practised without these specific details. In other instances, well known methods, procedures and/or components have not been described in detail so as not to obscure the invention.

The invention will be more clearly understood from the following description of the embodiments thereof, given by way of example only with reference to the accompanying drawings which are not drawn to scale.

Figure 1:
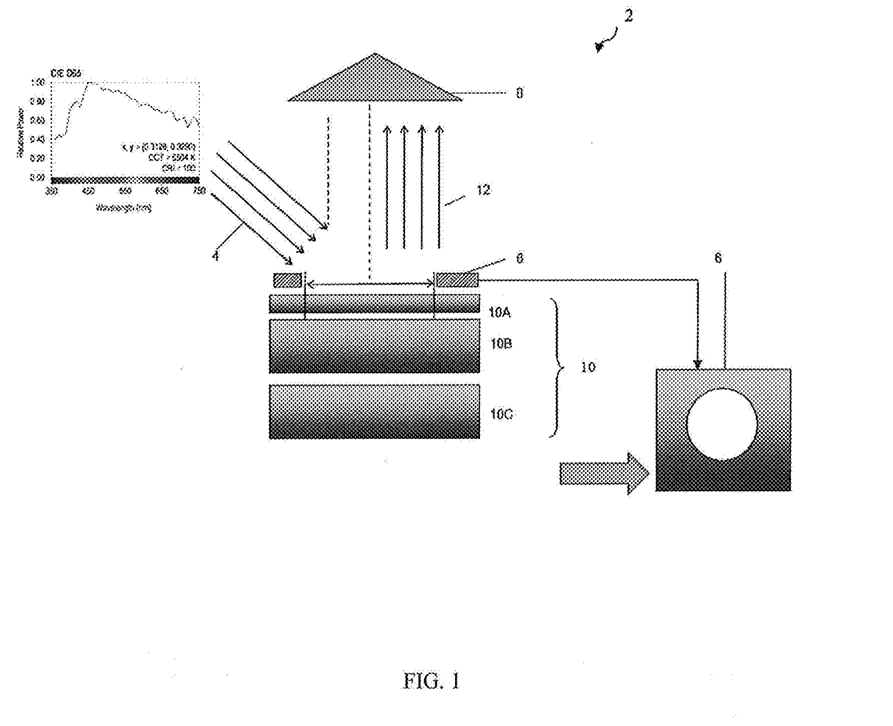
FIG. 1 is a schematic view of a visible light intensity sensing device employed in the present invention for measuring actual spectral reflectance.
Figure 2:
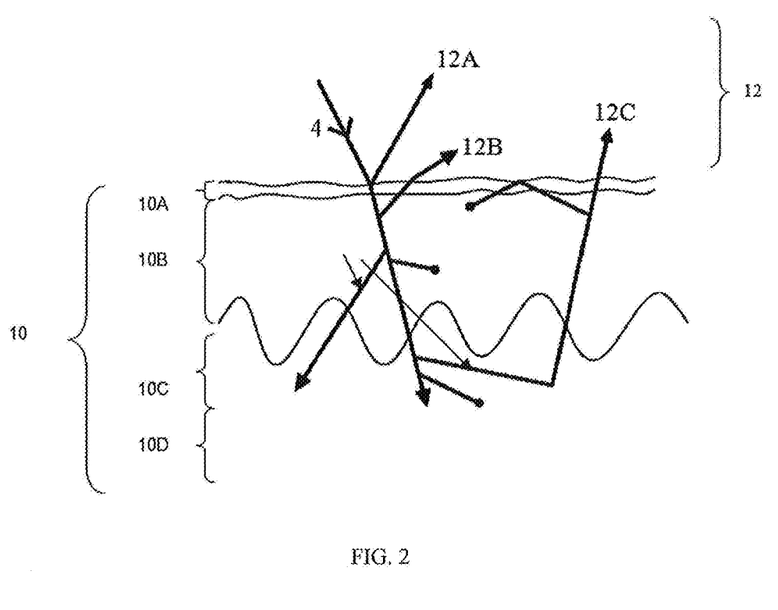
FIG. 2 is a schematic cross sectional view through a layer of skin illustrating the structure of the skin and the interaction of that structure with incident light.
Figure 3:
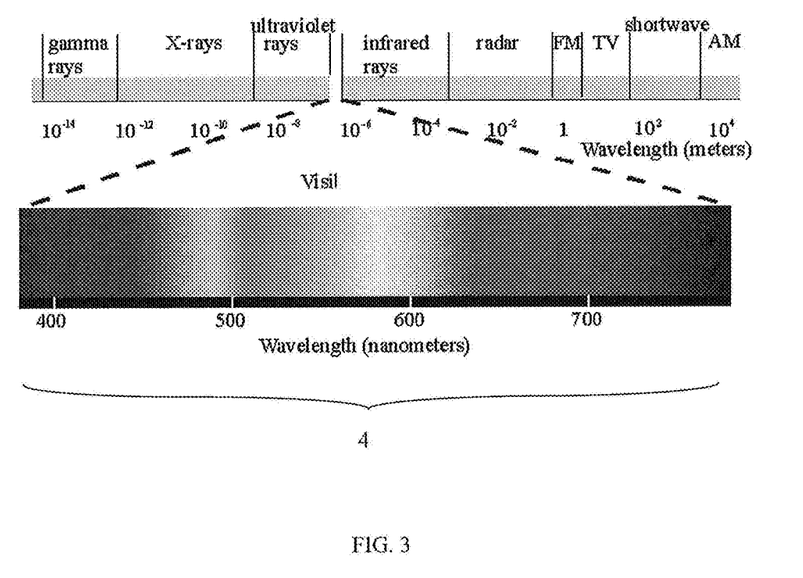
FIG. 3 illustrates a diagrammatic view of the electromagnetic spectrum showing the wavelengths of light together.

Referring to FIG. 1, there is shown a visible light intensity sensing device (2) employed in the present invention for measuring actual spectral reflectance (12) of skin when visible light falls on it. The visible light intensity sensing device (2) comprises at least a light source generating wavelengths of the electromagnetic spectrum for visible light (4), an adjustable aperture (6) and at least a recording device (8). The visible light intensity sensing device (2) may be a multispectral camera. Preferably the aperture is 7 millimeters in size but it is to be understood that other sizes are applicable as what is advantageous is the aperture assists to focus the light on a medium of study that is a particular area of the skin. The adjustable aperture (6) is placed between the human skin (10) and visible light (4). Prior to explaining further, the physical structure of the skin (10) and interaction of the skin (10) with light will be described briefly. The visible light intensity sensing device (2) may alternatively be a spectrophometer (not shown). Referring now to FIG. 2, there is shown a schematic cross sectional view through layers of skin (10) illustrating the structure of the skin and the interaction of that structure with incident light. As shown in FIG. 2, the skin (10) is a layered structure comprising four layers namely the stratum corneum (10A), the epidermis (10B), the dermis (10C) and the hypodermisy (10D). When visible light (4) from the earth's electromagnetic spectrum or as generated passes through the apertured plate (6) and falls on a human skin surface at an angle, the following incidents occur, it can either be absorbed (and scattered) or reflected as illustrated in FIG. 2. Referring to FIG. 3, there is illustrated a diagrammatic view of the earth's electromagnetic spectrum showing the wavelengths of light together. Visible light (4) is light that is visible to and can be detected by the human eyes and comprises the portion of electromagnetic radiation that lies near the middle of the spectrum from violet at about 380 nanometers (nm) to deep red at about 750 nm [1 nm=$10^{-9}$ m]. The entire spectrum illustrated in FIG. 3 measures the wavelengths of different types of electromagnetic radiation. Electromagnetic radiation is energy comprising small particles which scientists call photons having packs of energy moving in a wave pattern. Scattering is defined as any process in which the propagation of light is altered from its original angle. Absorption is the loss of light photon when its energy is invested in transition within an atom or molecule. A proportion of the visible light (4) is immediately reflected by the stratum corneum (10A) as actual reflected light and a proportion of light that is not immediately reflected does pass through the stratum corneum (10A) region and proceeds to interact with the constituents of the skin, namely the stratum corneum (10A), epidermis (10B) and the dermis (10C). In visible light (4) absorption of light photons is by the chromophores. Chromophore is that part of the molecule that is responsible for colour. The stratum corneum (10A) is of a thickness ranging from 0.01 to 0.03 millimeters (mm) and as light passes through it, the chromophore responsible for propagating and absorbing light is beta carotene. The epidermis (10B) is of a thickness ranging from 0.05 to 0.1 mm and as light passes through it, the chromophore responsible for propagating and absorbing light is melanin and beta carotene. The dermis (10C) is much thicker and its thickness ranges from 0.6 mm to 3 mm and as light passes through it, the chromophore responsible for propagating and absorbing light is haemoglobin, bilirubin and beta carotene. The hypodermis is of a thickness up to 30 mm and there are no chromophores present in the hypodermis but the white fat reflects most of the visible light (4) [Meglinsky, 2001]. Below is a table illustrating the type of chromophore that is responsible for absorbing light at various region of the skin layer: —

| Skin Layer | Thickness (mm) | Chromophores |
|---|---|---|
| Stratum Corneum | 0.01-0.03 | Bete carotene |
| Epidermis | 0.05-0.1 | Melanin, Beta Carotene |
| Dermis | 0.6-3 | Haemoglobin, Bilirubin, Beta Carotene |
| Hypodermis | Up to 30 | Nil |

Figure 4:
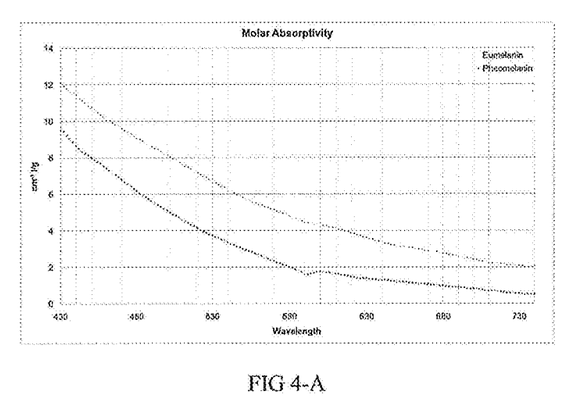

Each chromophore has different molar absorptive characteristics. Referring now to FIGS. 4-A to 4-C, there are shown graphic representations of skin absorption profile of different chromophores. For example maximum molar absorptivity for melanin types namely eumelanin and pheomelanin is as shown in FIG. 4-A at the lowest wavelength of the spectrum, for deoxy-haemoglobin the maximum molar absorptivity is as shown in FIG. 4-B at the wavelengths of about 430 nm and for deoxy-haemogloblin at the wavelengths of about 430 nm of the spectrum (please confirm this is correct); for beta-carotene, the maximum molar absorptivity is as shown in FIG. 4-C at the wavelength of about 450 nm of the spectrum and for bilirubin the maximum molar absorptivity is as shown in FIG. 4-C at the wavelength of about 455 nm of the spectrum.

Some light is also remitted after interacting with the chromophores present in the epidermis (10B) and dermis (10C) and the actual remitted light from the epidermis (10B) and dermis (10C) is also called actual epidermal remittance (12B) and actual dermal remittance (12C) respectively. The outward appearance of the skin (10) can therefore be considered a mixture of the actual reflected light (12A) namely light that is immediately reflected upon reaching the human skin surface (10), the actual epidermal remittance (12B) and actual dermal remittance (12C) of light (the three types of light (12A) (12B) (12C) described hereof are hereinafter collectively called "the actual spectral reflectance" and indicated generally by the reference numeral (12). Each layer of skin (10) has different scattering co-efficient ($\mu_s$) and absorption coefficient ($\mu_a$). Scattering and absorption coefficient are defined as function of light wavelength and skin chromophores. As the actual spectral reflectance (12) is affected by skin absorption coefficient ($\mu_a$) and the skin absorption coefficient ($\mu_a$) is wavelength dependant and is a function of skin chromophores, the actual spectral reflectance (12) can be recorded by the recording device (8) as multi-spectral data for analysis to collect baseline data on skin optical properties. This data collected from different coloured tone people and from different parts of the body can be used as the basis for comparison with simulated spectral reflectance (18) [which will be described below] for estimating the level of the type of melanin pigment present in the human skin (10) particularly the eumelanin and pheomelanin.

Figure 5:
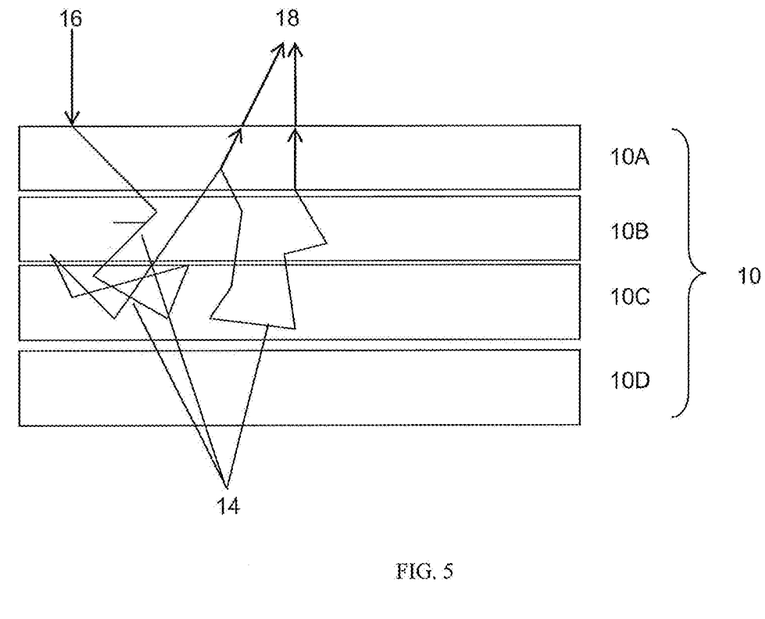
FIG. 5 shows a Monte Carlo Simulation of Light-Skin Interaction Model to simulate reflectance.

Referring to FIG. 5, there is shown a Monte Carlo Simulation of Light-Skin Interaction Model simulates reflectance. Monte Carlo Simulations are a class of computational algorithms that rely on repeated random sampling to compute their results. Monte Carlo methods are often used in simulating physical and mathematical systems. These methods are most suited to calculation by a computer and tend to be used when it is infeasible to compute an exact result with a deterministic algorithm. This method is also used to complement the theoretical derivations. By knowing the contribution of eumelanin and pheomelanin to the skin absorption coefficient ($\mu_a$) and together with scattering coefficients ($\mu_s$) and skin thickness, an accurate model of light interaction with skin tissue can be developed. In FIG. 5, the path (14) of a photon (16) is simulated when it interacts with the human skin (10). Step size is defined as a variable between photon (16) position and equals $\ln(\xi)/(\mu_a+\mu_s)$ where $\xi$ is a random number and $\mu_a$ and $\mu_s$ are absorption and scattering coefficients. For example the step size, for the light-stratum corneum (10A) interaction is calculated as $\ln(\xi)/(\mu_{a1}+\mu_s)$; the step size for light-epidermis (10B) interaction is calculated as $\ln(\xi)/(\mu_{a2}+\mu_s)$ and the step size light-dermis (10C) interaction is calculated as $\ln(\xi)/(\mu_{a3}+\mu_s)$. The weight (W) of photon (16) is decreased from an initial value of 1 as it moves through the skin layers, and equals a$^n$ after n number of steps, where a is the albedo (a=$\mu_s/((\mu_a+\mu_s)$)]. The value of g which is the anisotrophy factor of scattering is used to decide an angle deflection. When the photon (16) strikes the skin surface, a fraction of the photon (16) weight escapes as reflectance and the remaining weight is internally reflected and continues to propagate. The ratio between the sum of weights that escapes from the surface and the sum of initial weights used in the simulation gives the diffused reflectance or simulated reflectance (18).

Figure 6:
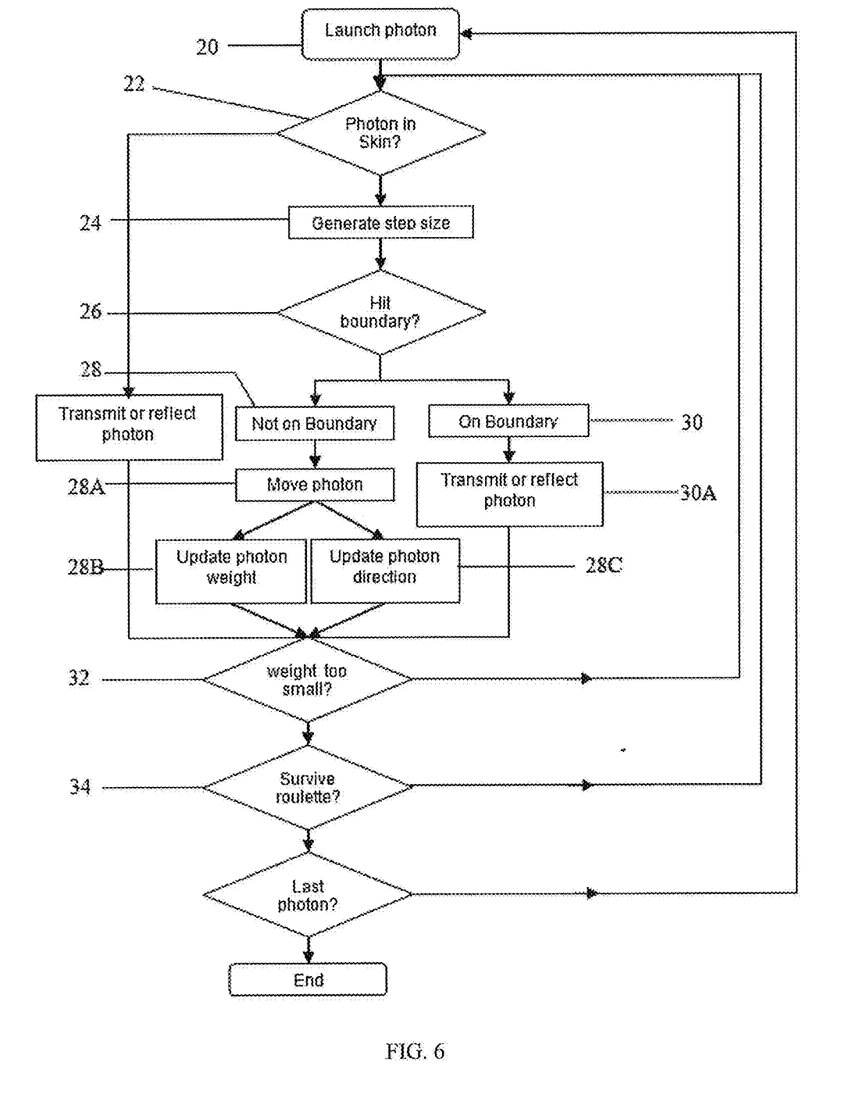
FIG. 6 shows a flow chart of the Monte Carlo Simulation of Light-Skin Interaction.

FIG. 6 shows a flow chart of the Monte Carlo Simulation of Light-Skin Interaction. This simulation of photon transport (light transport) in multi-layered tissue is performed using Monte Carlo simulation first developed by Prahl and Wang [Wang 1995]. The first step indicated by the reference numeral (20) is the initialisation step to launch a photon (16) from a photon discharging port towards skin (10). The second step indicated by the reference numeral (22) is to ascertain whether the photon (16) is in the skin or not. If the photon (16) is not in the skin, it is assumed that the photon is in the air or on the skin surface. Therefore the photon is transmitted or reflected If the photon (16) is in the skin then the third step indicated by the reference numeral (24), is triggered to generate step-size for each layer of the skin. The formula for generating step size is as stated above that is $\ln(\xi)/(\mu_a+\mu_s)$ where $\xi$ is a random number and $\mu_a$ and $\mu_s$ are absorption and scattering coefficients. Then a predetermined algorithm will check whether the photon (16) is on the boundary between skin layers or not as illustrated in the fourth step indicated by the reference numeral (26). If the photon is not on the boundary as shown in the first sub-step indicated by reference numeral (28), the position of the photon (16) is changed as shown in the step indicated by reference numeral (28A) achieved by updating the photon weight as illustrated by reference numeral (29A) and updating the photon direction as illustrated in reference numeral (29B). If the photon (16) is on the boundary as illustrated in second sub-step indicated by reference numeral (30), the photon (16) is transmitted or reflected as indicated in the step illustrated by reference numeral (30A). The fifth step indicated by reference numeral 32 is to test whether the weight of the photon (16) is too small or not. If the weight is not too small then it will be directed to the second step (22) where the processes from the second step (22) will be repeated. If the weight is too small, a termination process called roulette is performed. In the roulette, if the photon (16) does not survive, the process will end if it is the last photon (16) as illustrated in the sixth step indicated by reference numeral (34). If the photon survives, it will be back to the second step where the processes from the second step (22) are repeated.

Figure 7:
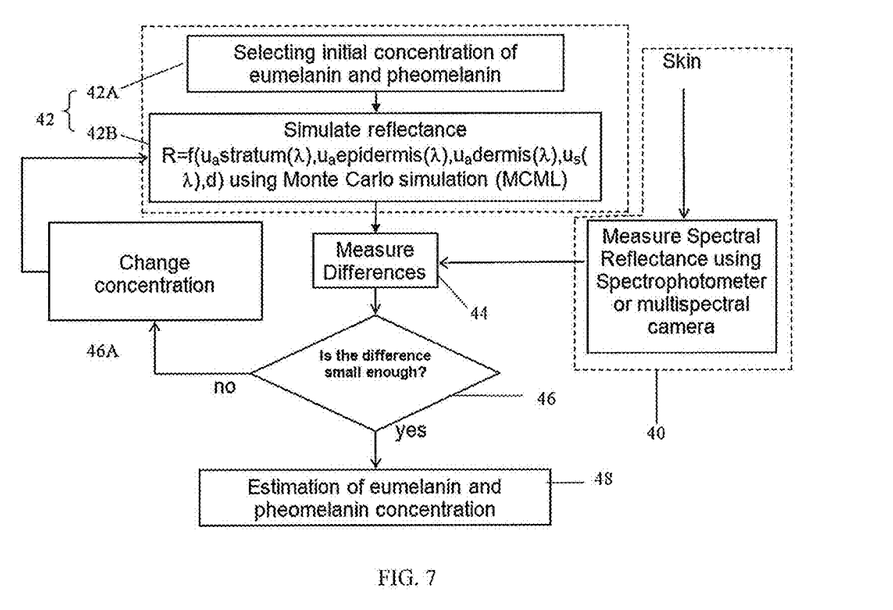
FIG. 7 is a flow chart of an inverse model for analysis of skin of the present invention.

Referring to FIG. 7 there is shown a flow chart of an inverse model for estimating the concentration of the type of melanin pigment, either eumelanin or pheomelaninin in the skin (10). In FIG. 7, the first inverse model step indicated by the reference numeral (40) is to measure actual spectral reflectance (12) of skin (10) using visible light intensity sensing device (2) which may be a spectrophotometer or a multispectral camera and recording the multi-spectral data in a recording device (8) for retrieval when required [This is similar to the steps illustrated in FIG. 1 for multispectral camera]. The second inverse model step indicated by the reference numeral (42) involves the primary sub-step (42A) of selecting initial concentration of the type of melanin pigment, either eumelanin and pheomelanin concentration and the secondary sub-step (42B) to simulate and record spectral reflectance (18) using the Monte Carlo simulation of Light-Skin interaction [This is similar to the steps in FIG. 5]. The simulation employs known equation that is $$SR=f(u_a\text{stratum}(l),u_a\text{epidermis}(l),u_a\text{dermis}(l),u_s(l),d)$$
where, SF is simulated reflectance;
$u_a$stratum(l) is absorption coefficient of the stratum corneum;
$u_a$dermis(l) is absorption coefficient of the epidermis;
$u_s(l)$ is the scattering coefficient
d is the thickness of skin layers
l is the wavelength of the light spectrum The third inverse model step indicated by the reference numeral (44) compares and measures the difference between data on actual spectral reflectance (12) collected from the visible light intensity sensing device (2) which may be a spectrophotometer or the multispecral camera and data simulated from the said Monte Carlo simulation. The fourth inverse model step indicated by the reference numeral (46) is to determine the difference from the said comparison. If the difference is smaller than an acceptable level, then the concentration of the type of melanin pigment, either eumelanin or pheomelanin will be estimated in the fifth inverse model step indicated by the reference numeral (48). If on the other hand the difference is larger than an acceptable level, then the concentration of the eumelanin or pheomelanin is altered in the sub-step indicated by the reference numeral (46A) and sent to undergo the whole process starting from the second inverse model step (42), that is from the Monte Carlo simulation stage. This process is repeated until the difference obtained is smaller than an acceptable level whereupon the concentration of the types of melanin pigment, either eumelanin and pheomelanin will then be estimated.

A skin pigmentation computer model can then be developed based on analysis of types of melanin (eumelanin or pheomelanin) of baseline data. The analyses of the types of melanin pigment either eumelanin and pheomelanin (skin pigmentation anaylsis) is performed based on the developed skin pigmentation computer model.

While the preferred embodiment of the present invention and its advantages has been disclosed in the above Detailed Description, the invention is not limited thereto but only by the scope of the appended claim.

What is claimed is:

1. A method for determining a concentration of melanin pigment in human skin comprising:
    a) measuring actual spectral reflectance of skin using a visible light intensity sensing device and recording multi-spectral data using a recording device for retrieval;
    b) selecting an initial concentration of a type of melanin pigment;
    c) simulating spectral reflectance using a Monte Carlo simulation, and recording the spectral reflectance simulated from the Monte Carlo simulation;
    d) comparing and measuring a difference between data of the actual spectral reflectance collected from the visible light intensity sensing device and data of the spectral reflectance simulated from the Monte Carlo simulation;
    e) determining if the difference between the data of the actual spectral reflectance collected from the visible light intensity sensing device and the data of the spectral reflectance simulated from the Monte Carlo simulation is smaller than an acceptable level;
    f) altering a concentration of the type of melanin pigment if the difference is larger than an acceptable level;
    g) repeating steps c), d), e) and f) until the difference between the data of the actual spectral reflectance collected from the visible light intensity sensing device and the data of the spectral reflectance simulated from the Monte Carlo simulation is smaller than an acceptable level;
    h) estimating the concentration of the type of melanin pigment.

2. The method of claim 1, wherein the visible light intensity sensing device is a spectrophometer.

3. The method of claim 1, wherein the visible light intensity sensing device is a multispectral camera.

4. The method of claim 1, wherein the type of melanin pigment applicable is eumelanin or pheomelanin.

5. The method of claim 1, wherein the method is non-invasive.

6. The method of claim 1, wherein the method is an in vivo method.

* * * * *